United States Patent

Ogawa et al.

Patent Number: 5,202,452
Date of Patent: Apr. 13, 1993

[54] TERMINAL PERFLUOROALKYLSILANE COMPOUND AND A PROCESS FOR PREPARING THE SAME

[75] Inventors: Kazufumi Ogawa, Hirakata; Norihisa Mino, Settsu; Toshinobu Ishihara, Joetsu; Mikio Endo, Joetsu; Tohru Kubota, Joetsu; Yasuhisa Tanaka, Yokohama, all of Japan

[73] Assignees: Matsushita Electric Industrial Co., Ltd., Osaka; Shin-Etsu Chemical Co., Ltd., Tokyo, both of Japan

[21] Appl. No.: 753,522

[22] Filed: Sep. 3, 1991

[30] Foreign Application Priority Data

Sep. 7, 1990 [JP] Japan .................................. 2-237531

[51] Int. Cl.$^5$ .............................................. C07F 7/12
[52] U.S. Cl. ..................... 556/435; 556/418; 556/454
[58] Field of Search .................... 556/435, 418, 454

[56] References Cited

U.S. PATENT DOCUMENTS

| | | | |
|---|---|---|---|
| 3,146,251 | 8/1964 | Brown et al. | 556/454 |
| 4,658,049 | 5/1987 | Nakano et al. | 556/437 |
| 4,992,521 | 2/1991 | Saho et al. | 556/454 X |
| 5,028,679 | 7/1991 | Terae et al. | 556/435 X |

*Primary Examiner*—Arthur C. Prescott
*Attorney, Agent, or Firm*—Panitch, Schwarze, Jacobs & Nadel

[57] ABSTRACT

A silane compound represented by the following general Formula (I) is described:

$$F(CF_2)_m(CH_2)_nA(CH_2)_pSiX_{3-q}R^1_q \quad (I)$$

wherein
$R^1$ is an alkyl group with 1 to 4 carbon atoms;
A is oxygen atom (—O—), carboxyl group $$(-\overset{O}{\underset{\|}{C}}-O-),$$

or an alkylsilylene group $$(-\underset{R^3}{\overset{R^2}{\underset{|}{Si}}}-);$$

wherein each $R^2$ and $R^3$ is an alkyl group with 1 to 4 carbon atoms;
x is a halogen atom, or an alkoxyl group;
m is an integer from 1 to 8;
n is an integer from 0 to 2;
p is an integer from 5 to 25; and
q is an integer from 0 to 2.

The silane compound is useful as a coating agent for various base materials, to provide lubricity, in addition to stain-proofing property.

2 Claims, No Drawings

TERMINAL PERFLUOROALKYLSILANE COMPOUND AND A PROCESS FOR PREPARING THE SAME

BACKGROUND OF THE INVENTION

1. Field of the Invention

The present invention relates to a novel terminal perfluoroalkylsilane compound useful as a coating agent for various base materials, especially a coating agent that provides lubricity, in addition to stain-proofing property, and to a process for preparing the same.

2. Description of the Prior Art

A lubricant layer is formed on a conventional magnetic recording medium such as a magnetic disc, a magnetic tape, or the like, in order to reduce the friction which occurs when they are used. The lubricant layer is formed by coating a lubricant on the magnetic film of the magnetic recording materials.

The lubricant is normally in a liquid form, and contains silicone oil, fluorine-containing compounds, and the like. Therefore, when a magnetic tape is subject to a winding operation, there are several disadvantages in that the lubricant moves in a certain direction and is forced into certain places because of centrifugal force, or lubricating capability of the layer reduces because the lubricant has evaporated. To solve these problems, various lubricants having less vapor pressure have been used, but the same problems still occur.

Other methods to form a lubricant layer have been suggested comprising bonding various silane coupling agents, which are commercially available, to inorganic materials that are present on a magnetic film through a covalent bond. However, normally, the silane coupling agents that are commercially available have several problems. One of the problems is that the organic functional groups attached to the silica atoms are so short that the agents may not have sufficient lubricant effects. Another problem is that the side chains of the organic functional groups may twist each other, or when other than carbon atoms such as nitrogen, oxygen, or sulfur atoms, etc., are contained in the backbone of the organic functional group, the organic functional groups may twist together due to the change of their bond angles, so that a uniform lubricant layer cannot be formed.

SUMMARY OF THE INVENTION

The silane compound of this invention, which overcomes the above-discussed and numerous other disadvantages and deficiencies of the prior art, is represented by the following general Formula (I):

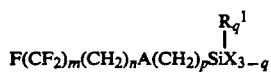   (I)

wherein
R$^1$ is an alkyl group with 1 to 4 carbon atoms;
A is an oxygen atom (—O—), a carboxyl group

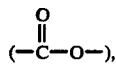

or an alkylsilylene group

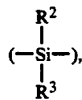

wherein each R$^2$ and R$^3$ is an alkyl group with 1 to 4 carbon atoms;
X is a halogen atom or an alkoxyl group;
m is an integer from 1 to 8;
n is an integer from 0 to 2;
p is an integer from 5 to 25; and
q is an integer from 0 to 2.

Also, the process for preparing the silane compound of this invention, which is represented by the following general Formula (I):

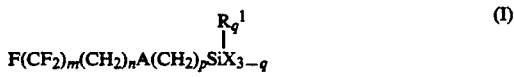   (I)

wherein
R$^1$ is an alkyl group with 1 to 4 carbon atoms;
A is an oxygen atom (—O—), a carboxyl group

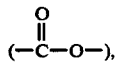

or an alkylsilylene group

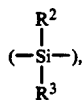

wherein each R$^2$ and R$^3$ is an alkyl group with 1 to 4 carbon atoms;
X is a halogen atom or an alkoxyl group;
m is an integer from 1 to 8;
n is an integer from 0 to 2;
p is an integer from 5 to 25; and
q is an integer from 0 to 2;
comprises reacting an alkene compound represented by the following general Formula (II):

$$F(CF_2)_m(CH_2)_nA(CH_2)_{p-2}CH=CH_2 \quad (II)$$

wherein A, m, n, and p are the same as defined hereinbefore in Formula (I),
with a silicon compound represented by the following Formula (III):

   (III)

wherein R$^1$, X, and q are as defined hereinbefore in Formula (I)
in a hydrosilylation reaction.

Thus, the invention described herein makes possible the objectives of (1) providing a compound useful as a coating agent which can provide lubricity, in addition to stain-proofing property;

(2) providing a compound suitable for the formation of a lubricant layer of ultra-thin film on the surface of a magnetic recording medium which has satisfactory lubricity, excellent adhesiveness and durability, when the compound is coated on the base materials;

(3) providing a silane coupling agent like compound which can be readily adsorbed onto the surface of base materials by a chemical adsorption technique to form the aforementioned thin film; and (4) providing the aforementioned compound which can be provided at low cost because of its easy preparation process.

DESCRIPTION OF THE PREFERRED EMBODIMENTS

The silane compound of this invention (a terminal perfluoroalkylsilane compound) is represented by the following general Formula (I):

$$F(CF_2)_m(CH_2)_nA(CH_2)_pSiX_{3-q}R^1_q \quad (I)$$

wherein
R$^1$ is an alkyl group with 1 to 4 carbon atoms;
A is oxygen atom (—O—), carboxyl group $$(-\overset{O}{\underset{\|}{C}}-O-),$$

or an alkylsilylene group $$(-\underset{\underset{R^3}{|}}{\overset{\overset{R^2}{|}}{Si}}-),$$

wherein each R$^2$ and R$^3$ is an alkyl group with 1 to 4 carbon atoms;
X is a halogen atom or an alkoxyl group;
m is an integer from 1 to 8;
n is an integer from 0 to 2;
p is an integer from 5 to 25; and
q is an integer from 0 to 2.

The compound can be obtained by reacting an alkene compound represented by the following general Formula (II):

$$F(CF_2)_m(CH_2)_nA(CH_2)_{p-2}CH=CH_2 \quad (II)$$

wherein A, m, n and p are as defined hereinbefore in Formula (I),
with a silicon compound represented by the following general Formula (III):

$$HSiX_{3-q}R^1_q \quad (III)$$

wherein R$^1$, X, and are as defined hereinbefore in Formula (I)
in a hydrosilylation reaction.

Examples of the alkene compounds (a terminal perfluoroalkene compound) represented by the above-described Formula (II) which is a raw material for preparing the compound (I) of this invention include the following compounds:

$$CF_3(CH_2)_2\underset{\underset{CH_3}{|}}{\overset{\overset{CH_3}{|}}{Si}}(CH_2)_{13}CH=CH_2$$

(15-(trifluoropropyldimethylsilyl)pentadecene), $$C_4F_9(CH_2)_2\underset{\underset{CH_3}{|}}{\overset{\overset{CH_3}{|}}{Si}}(CH_2)_7CH=CH_2$$

(9-(nonafluorohexyldimethylsilyl)nonene),
CF$_3$CH$_2$O(CH$_2$)$_{13}$CH=CH$_2$ (15-trifluoroethoxy)pentadecene),
CF$_3$COO(CH$_2$)$_{13}$CH=CH$_2$ (15-(trifluoroacetoxy)pentadecene).

Examples of the silicon compounds represented by the above-described Formula (III) include, for example, the following compounds:

HSiCl$_3$ (trichlorosilane), $$H\underset{}{\overset{\overset{CH_3}{|}}{Si}}Cl_2 \text{ (methyldichlorosilane)},$$

$$H\underset{}{\overset{\overset{(CH_3)_2}{|}}{Si}}Cl \text{ (dimethylchlorosilane)},$$

HSi(OCH$_3$)$_3$ (trimethoxysilane), $$H\underset{}{\overset{\overset{CH_3}{|}}{Si}}(OC_2H_5)_2 \text{ (methyldiethoxysilane)}.$$

The following are the examples of the terminal perfluoroalkylsilane compounds represented by the above-described Formula (I), which can be obtained by reacting the terminal perfluoroalkene compound with the silicon compound described hereinafter:

$$CF_3(CH_2)_2\underset{\underset{CH_3}{|}}{\overset{\overset{CH_3}{|}}{Si}}(CH_2)_{15}SiCl_3$$

(15-(trifluoropropyldimethylsilyl)pentadecyltrichlorosilane), $$C_4F_9(CH_2)_2\underset{\underset{CH_3}{|}}{\overset{\overset{CH_3}{|}}{Si}}(CH_2)_9\overset{\overset{CH_3}{|}}{Si}Cl_2$$

(9-(nonafluorohexyldimethylsilyl)nonylmethyl-dichlorosilane),

CF$_3$CH$_2$O(CH$_2$)$_{15}$Si(OCH$_3$)$_3$
(15-(trifluoroethoxy)pentadecyltrimethoxysilane), $$CF_3COO(CH_2)_{15}\overset{\overset{CH_3}{|}}{Si}(OC_2H_5)_2$$

(15-(trifluoroacetoxy)pentadecylmethyldiethoxysilane).

According to the process of this invention, the above-described $$CF_3(CH_2)_2\underset{\underset{CH_3}{|}}{\overset{\overset{CH_3}{|}}{Si}}(CH_2)_{15}SiCl_3$$

can be obtained by the following procedure:

A relatively inexpensive industrial raw material,

is reacted with a general methylation agent to form an intermediate,

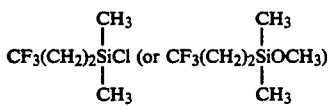

followed by the reaction of the intermediate with a Grignard reagent, $CH_2=CH(CH_2)_{13}Cl$ (pentadecenyl-chloride) to form

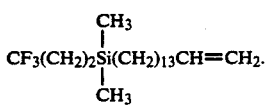

Then, the resulting product is further reacted with $HSiCl_3$ under the presence of a catalyst in a hydrosilylation reaction.

This hydrosilylation reaction is conducted by reacting a terminal perfluoroalkene compound with a silicon compound under the presence of a catalyst such as a platinum catalyst at the reaction temperature of 50° to 150° C. The reaction proceeds at reflux under atmospheric pressure, or in an airtight autoclave under superatmospheric pressure. Equivalent amounts of the terminal perfluoroalkene compound and the silicon compound can be reacted or an excess amount of the silicon compound can optionally be reacted with the terminal perfluoroalkene compound. The terminal perfluoroalkene compound is more expensive, thus the use of an excess amount of the silicon compound is desirable to react the terminal perfluoroalkene compound completely with to the silicon compound. The reaction mentioned above is conducted in the absence of a solvent, or in the presence of an unreactive solvent, including hydrocarbon solvents such as n-hexane, isooctane, toluene, xylene, and the like as needed.

After the reaction is completed, low volatile materials such as solvents and the unreacted compounds are stripped from the reaction mixture to obtain a crude compound (I). The crude compound (I) is pure enough to utilize, but if possible, it may be distilled to purify.

The resulting compound of this invention is coated on the surface of the base materials to form a film with lubricity, in addition to stain-proofing, water repellent, and oil repellent properties for any practical use. For example, a base material having functional groups such as OH group, $NH_2$ group, and the like is immersed into a solution of the compound in an organic solvent. n-Hexane, chloroform, carbon chlorides, and the like are used as the organic solvents. The solution may be coated by, for example, a spray method instead of immersing. The immersed, or sprayed base material is allowed to stand at room temperature, or heat-treated.

The treatments described above proceed the reaction between the aforementioned functional groups and the -Si-X portion of the compound (I), thereby the compound bonds to the surface of the base material through a siloxane bond by a chemical adsorption process to form a monomolecular film.

The film thickness of the monomolecular film (lubricant film) can optionally be controlled by adjusting the number of atoms of the compound (I), i.e., its chain length.

Since the compound (I) contains a fluoroalkyl group in its terminal portion, the molecules of the compound (I) become aligned such that the surface of the resulting monomolecular film has the fluorine atoms aligned together on the outermost surface. Therefore, the monomolecular film with lubricity, in addition to durability and stain-proofing and releasing properties can be obtained. The monomolecular film is useful as a lubricant layer formed on the surface of the magnetic layer of a magnetic recording medium such as a magnetic disc, magnetic tape, or the like. The film is also useful as a protecting layer for an optical fiber or a condenser.

The compound of this invention contains in its molecular chains hetero atoms or hetero groups such as oxygen atom, carboxyl group, dialkylsilylene group, or the like. Therefore, when the compound is chemically adsorbed onto the surface of a base material, the resulting monomolecular film will have high lubricity because the degree of freedom of the molecules become high. When the number of the methylene groups (p) between the hetero atom A and Si atom is small, the molecular chains may be twisted. However, because the number of the methylene groups (p) in the compound of this invention is 5 or more the molecular chains are not twisted, and chemically adsorbed onto the surface of a base material vertically, so that a uniform monomolecular film can be formed. The number (p) is 5 to 25, preferably 10 to 25. If (p) is more than 25, the molecular chains may also be twisted because of a long organic functional group attached to the silicon atom, so that a uniform monomolecular film cannot be formed.

As described above, when hetero atoms are contained in the functional groups bonded to the silicon atom, a uniform monomolecular film can also be formed. Therefore, the compound (II) can be produced with the use of inexpensive raw materials with the process of this invention. It is possible to prepare the compound (I) of this invention, which is produced from the compound (II), at low cost. When the compound of this invention is chemically adsorbed on a magnetic recording layer, a monomolecular film is formed through a strong siloxane bond between a -SiX group (hydrolysis group) and a magnetic layer or a protection layer on a magnetic layer. Therefore, the resulting monomolecular film (lubricant film) has extremely high durability because it is prevented from scattering or evaporating.

The examples of this invention are illustrated below. It is to be understood that the present invention is not limited to these examples.

EXAMPLES

Example 1

To a 300 ml glass flask that is equipped with a stirrer, a reflux condenser, a thermometer, and a dropping funnel, 0.5 mole of

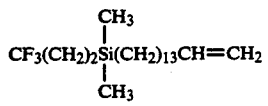

(15-(trifluoropropyldimethylsilyl)pentadecene) and 0.05 g of isopropyl alcohol solution that contains 20% H₂PtCl₆ 6H₂O were charged, and heated to 100° C. Then, 0.6 mole of HSiCl₃ (trichlorosilane) was added dropwise to the flask through the dropping funnel in the temperature range of 100° to 110° C. over 3 hours.

After the drip addition was completed, the mixture was heated at 110° to 120° C. for 2 hours to proceed with a reaction. The reaction solution was then cooled, and measured in a silicon capillary column by gas chromatography. The disappearance of the peak of 15-(trifluoropropyldimethylsilyl)pentadecene was identified according to the gas chromatography measurement.

Then, the reaction solution was distilled to obtain

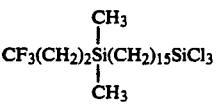
(15-(trifluoropropyldimethylsilyl)pentadecyltrichlorosilane),

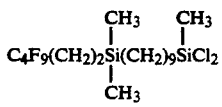
(9-(nonafluorohexyldimethylsilyl)nonylmethyl-dichlorosilane),

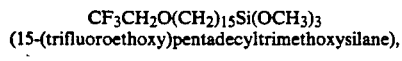
(15-(trifluoroethoxy)pentadecyltrimethoxysilane),

(15-(trifluoroacetoxy)pentadecylmethyldiethoxysilane).

(15-(trifluoropropyldimethylsilyl)) pentadecyltrichlorosilane) at the boiling point of 189° C./2 mmHg in a 89% yield.

Below, the data of the resulting compound is shown.

(1) GC-MS (m/Z) Electron Ionization Method: 443, 445 (molecule-HF-Cl). Chemical Ionization Method: (reactive gas: isobutane): 497, 499 (pseudo-molecular ion peak; molecule-H); (reactive gas: ammonium): 516, 518 (pseudo-molecular ion peak; molecule+NH₄).

(2) ¹H-NMR (δ ppm) (CHCl₃=7.26 ppm)

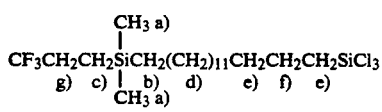

a)0.22(6H), b)0.54(2H), c)0.73(2H), d)1.29(22H), e)1.41(4H), f)1.58(2H), g)2.00(2H)

(3) ¹³C-NMR (δ ppm) (CDCl₃=77 ppm)

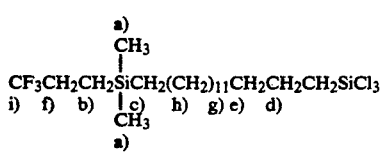

a)3.8, b)6.9, c)14.8, d)22.3, e)24.4, f)28.6, g)31.9, h)23.7, 29.1, 29.39, 29.42, 29.65, 29.65, 29.69, 29.73, 29.73, 29.77, 33.6, i)127.9(J$_{CF}$ 276.3 Hz)

Example 2

To a 500 ml glass flask that is equipped with a stirrer, a reflux condenser, a thermometer, and a dropping funnel, 250 ml of o-xylene, 0.05 g of a 20% isopropyl alcohol solution of H₂PtCl₆.6H₂O, and 0.45 mole of HSiCl₃ were charged, and heated to 85° C. Then, 0.3 mole of

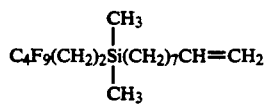

(9-(nonafluorohexyldimethylsilyl)nonene was added dropwise to the flask through the dropping funnel in the temperature range of 85° to 100° C. over 2 hours.

After the drip addition was completed, the mixture was heated at the temperature of 100° to 110° C. for 2 hours to proceed with a further reaction. Then, the reaction solution was cooled, and measured in a silicon capillary column by gas chromatography. The disappearance of the peak of 9-(nonafluorohexyldimethylsilyl)nonene was identified according to the gas chromatography measurement.

Then, the reaction solution was distilled to obtain

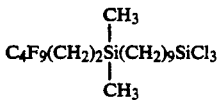

9-(nonafluorohexyldimethylsilyl)nonyltrichlorosilane at the boiling point of 164° C./1 mmHg in a 94% yield.

The following illustrate the data of the resulting compound.

(1) GC-MS (m/Z): Electron Ionization Method: 317, 319, 321 (molecule-C₄F₉C₂H₄). Chemical Ionization Method: (reactive gas: ammonium) 582, 584, 586 (pseudomolecular ion peak; molecule+NH₄).

(2) ¹H-NMR (δ ppm) (CHCl₃=7.26 ppm)

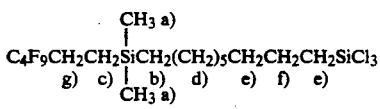

a)0.22(6H), b)0.54(2H), c)0.74(2H), d)1.30(10H), e)1.39(4H), f)1.58(2H), g)2.00(2H)

(3) ¹³C-NMR (δ ppm) (CDCl₃=77 ppm)

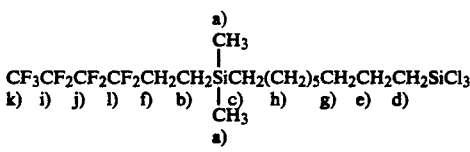

a)3.8, b)4.4, c)14.7, d)22.3, e)24.3, f)25.8, g)31.8, h)23.7, 29.0, 29, 29.3, 33.5, i)108.9(J$_{CF}$ 268.3H), j)110.8(J$_{CF}$264.3 Hz), k)117.5(J$_{CF}$ 288.13 Hz), l)118.3 (J$_{CF}$ 252.9 Hz)

Example 3

To a 300 ml glass flask that is equipped the same as in Example 1, 0.4 mole of CF₃CH₂O(CH₂)₁₃CH=CH₂ (15-(trifluoroethoxy) pentadecene), and 0.05 g of a 20% isopropylalcohol solution of H₂PtCl₆·6H₂O were charged, and heated to 110° C. Then, 0.6 mole of HSiCl₃ was added dropwise to the flask through the dropping funnel in the temperature range of 100° to 110° C. over 4 hours.

After the drip addition was completed, the mixture was heated at a temperature of 110° to 120° C. for 3 hours to proceed with a further reaction. The disappearance of the peak of 15-(trifluoroethoxy)pentadecene was identified according to the gas chromatography measurement.

Then, the reaction solution was distilled to obtain $CF_3CH_2O(CH_2)_{15}SiCl_3$ (15-(trifluoroethoxy) pentadecyltrichlorosilane) at the boiling point of 175° C./2 mmHg in a 82% yield.

The following illustrate the data of the resulting compound.

(1) IR (cm$^{-1}$): Major Absorbents: 2920, 2848(—CH$_2$—), 1155(C—O—C); Other Absorbents: 1460, 1305, 1275, 965, 822, 760, 715, 685, 660, 580, 560.

(2) GC-MS (m/Z): Electron Ionization Method: 342, 344, 346 (molecule-CF$_3$CH$_2$OH). Chemical Ionization Method: (reactive gas: isobutane): 441, 443, 445 (pseudo-molecular ion peak; molecule-H), 343, 345, 347 (molecule-CF$_3$CH$_2$O).

(2) $^1$H-NMR ($\delta$ ppm) (CHCl$_3$=7.26 ppm)

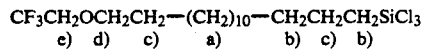

$CF_3CH_2OCH_2CH_2—(CH_2)_{10}—CH_2CH_2CH_2SiCl_3$
e)　d)　c)　　a)　　　b)　c)　b)

a)1.27(20H), b)1.40(4H), c)1.58(4H), d)3.59(2H), e)3.79(2H)

(3) $^{13}$C-NMR ($\delta$ ppm) (CDCl$_3$=77.0 ppm)

Example 4

The reaction procedure of Example 3 was repeated by the use of the same reaction vessel as in Example 3 except that $CF_3COO(CH_2)_{13}CH=CH_2$ (15-(trifluoroacetoxy) pentadecene was used.

After the reaction was completed, the reaction solution was distilled to obtain $CF_3COO(CH_2)_{15}SiCl_3$ (15-trifluoroacetoxy)pentadecyltrichlorosilane) at the boiling point of 170° C./2 mmHg in a 79% yield.

Below, the data of the resulting compounds are shown.

(1) IR (cm$^{-1}$): Major Absorbents: 2917, 2846(—CH$_2$—), 1780(C=O), 1215, 1158(C—O—C). Other Absorbents: 1460, 1398, 1342, 768, 720, 682.

(2) GC-MS (m/z): Electron Ionization Method: 387, 389, 391 (molecule-CF$_3$CO$_2$). Chemical Ionization Method: (reactive gas: isobutane): 445, 457, 459 (pseudomolecular ion peak; molecule-H), 421, 423 (molecule-Cl), 343, 345, 347 (molecule-CF$_3$CO$_2$).

(2) $^1$H-NMR ($\delta$ ppm) (CHCl$_3$=7.26 ppm)

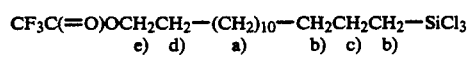

$CF_3C(=O)OCH_2CH_2—(CH_2)_{10}—CH_2CH_2CH_2—SiCl_3$
　　e)　d)　　　a)　　　b)　c)　b)

a) 1.26(20H), b)1.39(4H), c)1.56(2H), d)1.74(2H), e)4.34(2H).

(3) $^{13}$C-NMR ($\delta$ ppm) (CDCl$_3$=77.0 ppm)

Example 5

With the use of the compound of this invention as a chemical adsorbent, a monomolecular film was formed on the oxidized surface of an aluminum base plate according to the following procedure.

As a chemical adsorbent, 15-(trifluoropropyldimethylsilyl)pentadecyltrichlorosilane:

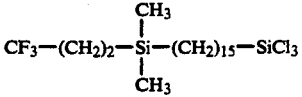

$$CF_3—(CH_2)_2—\underset{\underset{CH_3}{|}}{\overset{\overset{CH_3}{|}}{Si}}—(CH_2)_{15}—SiCl_3$$

was used. This chemical adsorbent was dissolved into cyclohexane in a concentration of 3 mmol/l. The aforementioned base plate was immersed into this solution over 60 minutes to form a monomolecular film.

According to the same procedure, monomolecular films were formed with the use of the following compounds as chemical adsorbents:
15-(trifluoroethoxy)pentadecyltrichlorosilane, $CF_3CH_2O(CH_2)_{15}—SiCl_3$;
15-(trifluoroacetoxy)pentadecyltrichlorosilane, $CF_3COO(CH_2)_{15}—SiCl_3$;
15-(trifluoroethoxy)pentadecyltrimethoxysilane, $CF_3CH_2O(CH_2)_{15}—Si(OCH_3)_3$;
15-(trifluoroacetoxy)pentadecylmethyldiethoxysilane,

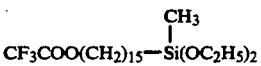

$$CF_3COO(CH_2)_{15}—\underset{|}{\overset{\overset{CH_3}{|}}{Si}}(OC_2H_5)_2$$

Example 6

The surface energy of the monomolecular film that is formed by chemically adsorbed $CF_3COO(CH_2)_{15}—SiCl_3$ prepared in Example 5 was about 20 dyn/cm. The surface energy of the monomolecular film of $CH_3(CH_2)_{19}SiCl_3$ prepared by the same procedure as in Example 5 was about 25 dyn/cm.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that residue in the present invention, including all features that would be treated as equivalents thereof by those skilled in the art to which this invention pertains.

What is claimed is:

1. A silane compound represented by the following general Formula (I):

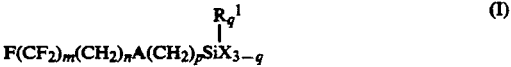

$$F(CF_2)_m(CH_2)_nA(CH_2)_pSiX_{3-q}\overset{R_q^1}{|} \quad (I)$$

wherein
R$^1$ is an alkyl group with 1 to 4 carbon atoms;
A is oxygen atom (—O—), carboxyl group

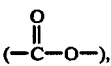

$$(—\overset{\overset{O}{\|}}{C}—O—),$$

or an alkylsilylene group

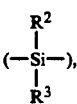

$$(—\underset{\underset{R^3}{|}}{\overset{\overset{R^2}{|}}{Si}}—),$$

wherein each $R^2$ and $R^3$ is an alkyl group with 1 to 4 carbon atoms;

X is a halogen atom or an alkoxyl group;

m is an integer from 1 to 8;

n is an integer from 0 to 2;

p is an integer from 5 to 25; and q is an integer from 0 to 2.

2. A process for preparing a silane compound represented by the following general Formula (I):

$$F(CF_2)_m(CH_2)_nA(CH_2)_p\overset{R^1_q}{\underset{|}{Si}}X_{3-q} \qquad (I)$$

wherein $R^1$ is an alkyl group with 1 to 4 carbon atoms;

A is oxygen atom (—O—), carboxyl group $$(-\overset{O}{\underset{\|}{C}}-O-),$$

or an alkylsilylene group $$(-\overset{R^2}{\underset{\underset{R^3}{|}}{Si}}-);$$

wherein each $R^2$ and $R^3$ is an alkyl group with 1 to 4 carbon atoms;

X is a halogen atom, or an alkoxyl group;

m is an integer from 1 to 8;

n is an integer from 0 to 2;

p is an integer from 5 to 25; and q is an integer from 0 to 2;

comprising reacting an alkene compound represented by the following general Formula (II):

$$F(CF_2)_m(CH_2)_nA(CH_2)_{p-2}CH=CH_2 \qquad (II)$$

wherein A, m, n and p are as defined hereinbefore in Formula (I), with a silicon compound represented by the following Formula (III):

$$\overset{R^1_q}{\underset{|}{H}SiX_{3-q}} \qquad (III)$$

wherein $R^1$, X, and q are as defined hereinbefore in Formula (I)

in a hydrosilylation reaction.

* * * * *